United States Patent [19]
Holland

[11] Patent Number: 5,577,910
[45] Date of Patent: Nov. 26, 1996

[54] VACUUM PUMP SEAL-WATER RECYCLING AND WASTE DISPOSAL SYSTEM FOR DENTAL OPERATORIES

[76] Inventor: Robert S. Holland, 31 High Ridge Rd., Redding, Conn. 06896

[21] Appl. No.: 250,025

[22] Filed: May 27, 1994

Related U.S. Application Data

[63] Continuation-in-part of Ser. No. 61,184, May 13, 1994, abandoned.

[51] Int. Cl.$^6$ ............................ A61C 17/06; A61C 17/14
[52] U.S. Cl. ................................................. 433/92
[58] Field of Search .................. 433/91, 92, 93, 433/94, 95, 96

[56] References Cited

U.S. PATENT DOCUMENTS

| | | | |
|---|---|---|---|
| 2,784,717 | 3/1957 | Thompson | 128/276 |
| 2,821,021 | 1/1958 | Winter | 433/92 |
| 3,988,134 | 10/1976 | Gandrud | 433/92 X |
| 4,293,300 | 10/1981 | Cattani | 433/92 |
| 4,344,756 | 8/1982 | Folkenroth et al. | 433/92 |
| 5,032,260 | 7/1991 | Alzner | 433/92 X |

*Primary Examiner*—Nicholas D. Lucchesi
*Attorney, Agent, or Firm*—Patrick J. Walsh

[57] ABSTRACT

A system for disposing of dental operatory effluent characterized by low water consumption for a water seal vacuum pump through the recycling of seal water, having means for controlling the temperature and vapor pressure of recirculating seal water, avoiding the presence of abrasives in seal water, reliable separation and disposal of gas-liquid-solid constituents of operatory effluent, collection and recovery of amalgam and heavy metals, and means for disinfecting the collection tank. Several embodiments of the invention are disclosed.

36 Claims, 6 Drawing Sheets

VACUUM PUMP SEAL-WATER RECYCLING AND WASTE DISPOSAL SYSTEM FOR DENTAL OPERATORIES

This application is a continuation-in-part of application Ser. No. 061,184 filed May 13, 1994, now abandoned.

BACKGROUND OF THE INVENTION

The present invention relates to dental operatories and in particular to vacuum disposal systems for removing waste from the oral cavity during dental operations. The invention is disclosed in alternative preferred configurations of water recycling and waste disposal system for dental operatories.

In the course of dental procedures such as drilling and filling or polishing teeth, conventional dental operatories provide for continuing evacuation from a patient's mouth of effluent containing saliva, water, pumice, amalgam, tooth chips, body tissue, and nitrous oxide when used in particular dental procedures. The operatory includes a vacuum tube placed in the patient's mouth to remove effluent as it is generated during the course of a procedure to a collection and disposal point within the dental office. The operating vacuum is produced by a water seal vacuum pump which requires a substantial water volume to maintain the pump seal in continuous operation throughout dental office hours. In an effort to reduce water consumption by the vacuum pump, conventional systems separate "gray water" from patient effluent and recycle the gray water to provide water sealing for the vacuum pump. Solids are screened from the effluent before entering the vacuum pump to provide a supply of gray water, and excess gray water is discharged to a disposal drain. A system of this kind includes a make-up water supply to augment the gray water supply so as to assure a proper water seal at all times for the operating vacuum pump. Water consumption of the vacuum system is determined by the volume of fresh make-up water required by the system on an hourly or daily basis.

U.S. Pat. No. 4,344,756 to Folkenroth et al. discloses a water recycler for dental operatories in which gray water from several office operatories is directed via a solids collector go the inlet side of twin vacuum pumps operating in parallel. The gray water is discharged from the vacuum pumps to a gas-water separator which functions also as a gray water reservoir. From the separator air is vented to atmosphere, gray water is recycled to the vacuum pump inlet, and excess gray water is discarded to a plumbing drain. A fresh water make-up feed system is operated intermittently to maintain the gray water reservoir at a prescribed level, and if necessary, to supply fresh water directly to the inlet side of the vacuum pumps.

U.S. Pat. No. 5,032,260 to Alzner discloses a system somewhat similar to Folkenroth for recycling gray water to provide a water seal for a dental operatory vacuum pump. In Alzner, gray water from the operatory passes a solids filter, enters the inlet of the vacuum pump and exits into a gas-liquid-solids separator. The gray water is recycled by means of a fresh water eductor which induces gray water flow from the separator into a commingled stream of gray/fresh sealing water. In an example of the invention, Alzner discloses fresh water usage of approximately ⅛ gpm or 7.5 gallons per hour.

The gas-liquids-solids separator disclosed in Alzner has an interior layout designed for minimizing the transfer of heat from the entrained gas to separated gray water so as to minimize unwanted increase in the vapor pressure of recycled water, a condition that is detrimental to optimum performance of the vacuum pump. Alzner also uses a greater amount of fresh water to make the eductor operate properly and to maintain the temperature of commingled sealing water at a suitable level for optimum vacuum pump performance.

Both of these patented systems rely on filters and separators to screen out solids and gas from operatory effluent to produce gray water as clean as possible. The filters and separators are effective to screen out larger particles such as amalgam and tooth chips, however, finer abrasive particles as well as tooth cleaning pumice are likely to pass through the filter along with the gray water recycling through the system and cause wear of vacuum pump water seals, impeller, and housing.

The emphasis in both Folkenroth and Alzner is to recover and recycle gray water for use as pump seal water. Both patents simply provide a solids filter or collector immediately before operatory effluent enters the vacuum pump. Screens or filters of very fine mesh adequate to screen out pumice from operatory effluent are prone to clogging thereby diminishing the efficiency of the vacuum system. To avoid loss of efficiency, larger mesh screens are selected to filter out larger solids, principally tooth chips and amalgam, while a significant portion of pumice is carried along with gray water through the screen into water pump seals. Pumice consists chiefly of silicates of aluminum, potassium, and sodium and abrades vacuum pump components gradually diminishing pump capacity. Accordingly, gray water recycling while improving water conservation does nonetheless less entail the disadvantage of increased vacuum pump wear.

European Patent No. 284,641 to Alkirk is of interest in pointing out that amalgam and other harmful metal compounds (mercury, silver, and tin) from dental surgeries require separation from mouth rinsing water for recovery of the heavy metals. Alkirk discloses such a system for separation and recovery.

The prior art includes other devices and techniques for separating and disposing of dental operatory effluent by using suction systems. These are U.S. Pat. Nos. 2,784,717 to Thompson, 2,821,021 to Winter, 3,988,134 to Gandrud, and 4,293,300 to Cattani. These patents are directed to maintaining system suction while separating and disposing of liquid and solid components of operatory effluent.

A suitable system for disposing of dental operatory effluent is characterized by low water consumption for a water seal vacuum pump through the recycling of seal water, means for controlling the temperature and vapor pressure of recirculating seal water, avoiding the presence of abrasives in seal water and consequential pump wear, reliable separation and disposal of gas-liquid-solid constituents of operatory effluent, collection and recovery of amalgam and heavy metals, and means for disinfecting the effluent. These matters are the subject of the present invention.

SUMMARY OF THE INVENTION

The present invention comprises a water recycling and waste disposal system for dental operatories utilizing a water seal vacuum pump for drawing effluent from a patient's mouth. In accordance with the invention, a collection tank is provided intermediate the vacuum pump and the operatory to receive the entire effluent from the patient. In a preferred form of the invention, the vacuum pump evacuates the collection tank and draws effluent from the operatory which is received and collected by the tank for periodic disposal.

In preferred embodiments of the invention, sealing water for the vacuum pump is contained in a closed circuit passing through the collection tank and having an inlet check valve for receiving air from the collection tank for cooling the recirculating seal water. The closed circuit includes a heat transfer inlet tube of sufficient length to allow transfer of the heat contained in the recirculating water to the cooling air passing through the pump. The heat transfer tube includes a vertical component acting as a very efficient heat exchanger because the passing air stream must carry the recirculating water vertically upward thereby allowing more intimate contact of air and water over a longer period of time, with increased heat transfer to the air. Gray water is not used for pump seals.

Fresh water make-up is provided directly to the vacuum pump shaft seal for augmenting sealing water and lubricating and cooling the shaft seal.

The recirculating water outlet from the vacuum pump passes to an improved gas-water separator which also serves as a reservoir for the recirculation water. The gas/water separator is configured to limit the loss of recirculation water. The undesirable condition of blow-by or carry-over of recirculating water to a drain line by cooling air racing through the separator is limited by separator design even for systems including twin 2 hp vacuum pumps operating at maximum air flow capacity. Cooling air containing the heat received from the recirculating water at the inlet heat exchanger is separated and vented to ambience through the gas/water separator. The separator also functions as an effective muffler for outlet flow from the vacuum pump by reason of separator size and configuration as well as its location within the collection tank.

The entire volume of operatory effluent collects in the tank provided. A sieve or mesh basket of proper porosity may be provided in the tank to trap solids especially amalgam and heavy metals discarded during the dental procedure.

The collection tank is fitted with a one-way drain check valve which is normally closed when the tank is evacuated by the vacuum pump. At the end of an operating day when the vacuum pump is secured, the check valve opens automatically under the influence of collected effluent which flows to a disposal drain. The check valve recloses when the system is again evacuated by the vacuum pump.

The collection tank is also provided with means for stopping air flow through the pump in the event of high effluent level in the collection tank, i.e., effluent rising to the level of the inlet check valve of the air inlet to the recirculating water circuit. For this purpose a light weight plastic ball floats in the effluent or is suspended from the tank cover in close proximity to the inlet check valve and is drawn to block the air inlet when the effluent level reaches inlet level.

Another aspect of the invention is to provide means for disinfection of the effluent. For this purpose a disinfectant, such as chlorine in the form of tablets or an elongated rod, is suspended within the tank for gradual dissolution in the presence of each batch of effluent collected within the tank.

In a modified form of the invention, a collection tank is evacuated by a water seal vacuum pump for drawing effluent from one or more dental operatories. The water seal for the pump comprises a closed circuit of recirculating seal water using no gray water. The closed circuit is provided with an eductor actuated by pressurized fresh make up water for inducing circulation of the seal water. The circuit is also provided with an air/water heat exchanger in which air at ambient temperature is evacuated by the vacuum pump from the operatories through the collection tank for cooling recirculating seal water. With this arrangement, cooling of the recirculating water is achieved by the air/water heat exchanger and the need for make-up fresh water is limited to the requirements for eductor operation and for maintaining the proper operating volume of sealing water in the closed circuit.

In another modified form of the invention, a collection tank is evacuated by a water seal vacuum pump for drawing effluent from one or more dental operatories. The water seal for the pump comprises a closed recirculating seal water circuit provided with a gas-water separator at the seal water outlet from the vacuum pump. The gas-water separator also functions as a reservoir for recirculating seal water to maintain an adequate supply of seal water for recirculation while discarding excess seal water to a plumbing drain. In addition, the separator is structurally apart from the collection tank. The circuit is also provided with an air/water heat exchanger in which air at ambient temperature is evacuated by the vacuum pump from the operatories through the collection tank for cooling recirculating seal water. This embodiment also includes a vacuum relief valve in the vacuum line from the operatories to the collection tank for the purpose of maintaining system vacuum within prescribed limits so as to have adequate vacuum draw when all dental operatories are operating, and to avoid high vacuum draw when only a single operatory is in use.

In another modified form of the invention, a remote collection tank is evacuated by a water seal vacuum pump for drawing effluent from one or more dental operatories. The collection tank is fitted with angled pipes to promote separation by cyclonic rotation of entrained sediments from the liquid portion of operatory effluent. The water seal for the pump comprises a closed circuit of recirculating seal water located outside the collection tank. A gas-water separator at the seal water outlet from the vacuum pump also functions as a reservoir for recirculating seal water to maintain an adequate supply of seal water for recirculation while discarding excess seal water to a plumbing drain. In addition, the gas-water separator is structurally apart from the collection tank. The circuit includes an air/water heat exchanger in preferred vertical orientation in which air at ambient temperature is evacuated by the vacuum pump from the operatories through the collection tank for cooling recirculating seal water. This embodiment also includes a vacuum relief valve in the vacuum line from the operatories to the collection tank for the purpose of maintaining system vacuum within prescribed limits so as to have adequate vacuum draw when all dental operatories are operating, and to avoid high vacuum draw when only a single operatory is in use.

In a further modified form of the invention, a collection tank is evacuated by a water seal vacuum pump for drawing effluent from one or more dental operatories. The water seal for the pump comprises a closed circuit of recirculating seal water including a reservoir within the collection tank for receiving seal water from the vacuum pump outlet and for directing excess air and water to a gas-water separator also located within the collection tank. The separator directs gas to ambiance through a vent, and excess water to a plumbing drain through a float valve. The circuit is also provided with an air/water heat exchanger in which air at ambient temperature is evacuated by the vacuum pump from the operatories through the collection tank for cooling recirculating seal water.

In another embodiment of the invention substantially similar in overall construction to FIG. 1, the seal water reservoir at the outlet from the vacuum pump is fitted with a float valve for discarding excess seal water to a plumbing drain. In addition the closed circuit for recirculating seal water is provided with a metering valve at the seal water inlet to the heat exchanger. The metering valve regulates the volume of recirculating seal water entering the heat exchanger.

In another embodiment of the invention, a single tank is partitioned into upper and lower chambers with the upper chamber serving as a combination reservoir and gas-water separator and the lower chamber serving as an evacuated collection tank. The seal water inlet to the heat exchanger is located within the reservoir (upper) chamber and is fitted with a metering valve. Additionally, a float valve within the reservoir maintains the recirculating seal water within prescribed limits and discards excess seal water to a plumbing drain. An air vent opens the upper chamber to ambience to vent air evacuated by the vacuum pump.

In another embodiment of the invention, a single tank is partitioned into upper and lower chambers with the upper chamber serving as a combination reservoir and gas-water separator and the lower chamber serving as a evacuated collection tank. The reservoir recirculating water level is maintained by an air-water separator opening in the reservoir wall for draining excess recirculating water, and for venting evacuated air to ambience. An air evacuation line from collection chamber to vacuum pump inlet passes through the reservoir in the form of a cooling coil for cooling recirculating water in the reservoir. The seal water inlet to the air-water heat exchanger is located within the reservoir chamber and is fitted with a metering valve. Additionally, a float valve maintains a positive quantity of seal water over the outlet to a plumbing drain to avoid air venting through the plumbing drain.

The modified embodiments of the invention shown in FIGS. 3–8 all include a ball float valve as part of the gas-water separator. The ball float valve provides very positive and complete separation of gas and water components included in the outflow from the vacuum pump. Nitrous oxide is widely used in dental procedures, is exhaled by the patient, and is drawn into the effluent evacuated from the patient's mouth. The ball float valve allows excess seal water only to enter the plumbing drain in that the valve closes with low water in the valve housing so that none of the evacuated air with entrained nitrous oxide enters the drain. In the low water condition, the valve is closed and the air/gas component of vacuum pump outflow can only rise through the vent to ambience. As excess seal water fills the valve housing, the ball floats opening the valve for draining the excess seal water. Excess seal water filling the valve housing while the valve is open, acts as an effective barrier to air/gas flow through the valve to drain. In this way, the ball float valve provides positive and complete separation of gas and water regardless of variations in the respective volumes of the gas and water constituents in the vacuum pump outflow. It should be noted in this regard that nitrous oxide in the drain system of the dental building is undesirable in that it is an explosive hazard, and that the gas can migrate through the plumbing system, exit through sink drains and possibly be inhaled inadvertently by someone using the sink.

Accordingly, the present invention provides a simplified water recycling and waste disposal system which improves water consumption over conventional devices without use of gray water, eliminates the presence of abrasives in seal water, utilizes ambient air drawn into the system by the vacuum pump for cooling recirculating seal water to maintain its temperature and vapor pressure within proper limits for optimum vacuum pump performance, provides for reliable and automatic waste disposal, allows for retrieval of recyclable solids especially heavy metals from a collection sieve, extends useful pump life, meters flow of recirculating seal water into the air-water heat exchanger, vents evacuated air and gas to ambience and discards excess seal water to drain, and provides a germicide within the waste collection system.

OBJECTS OF THE INVENTION

It is an object of the invention to provide a simplified water recycling and waste disposal system for dental operatories.

It is an object of the invention to provide a waste disposal system for dental operatories utilizing a water seal vacuum pump with improved water consumption rates.

It is a further object of the invention to provide a waste disposal system for dental operatories organized about a collection tank which is evacuated by a water seal vacuum pump to collect the entire effluent from a patient's mouth during a dental procedure, with an air cooled closed water seal circuit for the vacuum pump and with fresh water make-up supplied directly to the pump seals.

It is another object of the invention to provide for transfer of heat from recirculating water to evacuated air by intimated, prolonged contact of water and air flowing to the vacuum pump inlet thereby maintaining the vapor pressure of recirculating within proper limits for optimum vacuum pump operation.

It is a further object of the invention to provide an alternate to the conventional use of gray water for water seal of vacuum pumps while consuming less make-up seal water than gray water systems, and avoiding abrasives in the seal water which reduce pump life.

It is a further object of the invention to provide a porous receptacle within the collection tank for retaining recoverable materials such as amalgam, heavy metals and so forth entrained in the operatory effluent.

It is a further object of the invention to provide means for disinfecting the effluent in normal use.

It is another object of the invention to provide a waste disposal system for dental operatories incorporating an evacuated collection tank for receiving and holding the entire effluent from one or more operatories in a dental office during the course of a day, and for automatically discarding retained effluent by shutting down the vacuum pump used for evacuating the collection tank.

It is another object of the invention to provide metering of recirculating seal water into the air water heat exchanger.

It is another object of the invention to provide control of discarding seal water to a plumbing drain.

It is another object of the invention to provide a variety of configurations for efficient operation of the water seal recirculation aspects of the invention.

It is another object of the invention to provide for maintaining system vacuum at appropriate operating level according to the number of operatories in use at a given moment.

It is another object of the invention to provide very positive and complete separation of gas and water components included in the outflow from the vacuum pump such that gas vents to ambience and does not enter plumbing drains.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which.

DETAILED DESCRIPTION OF THE INVENTION

Figure 1:
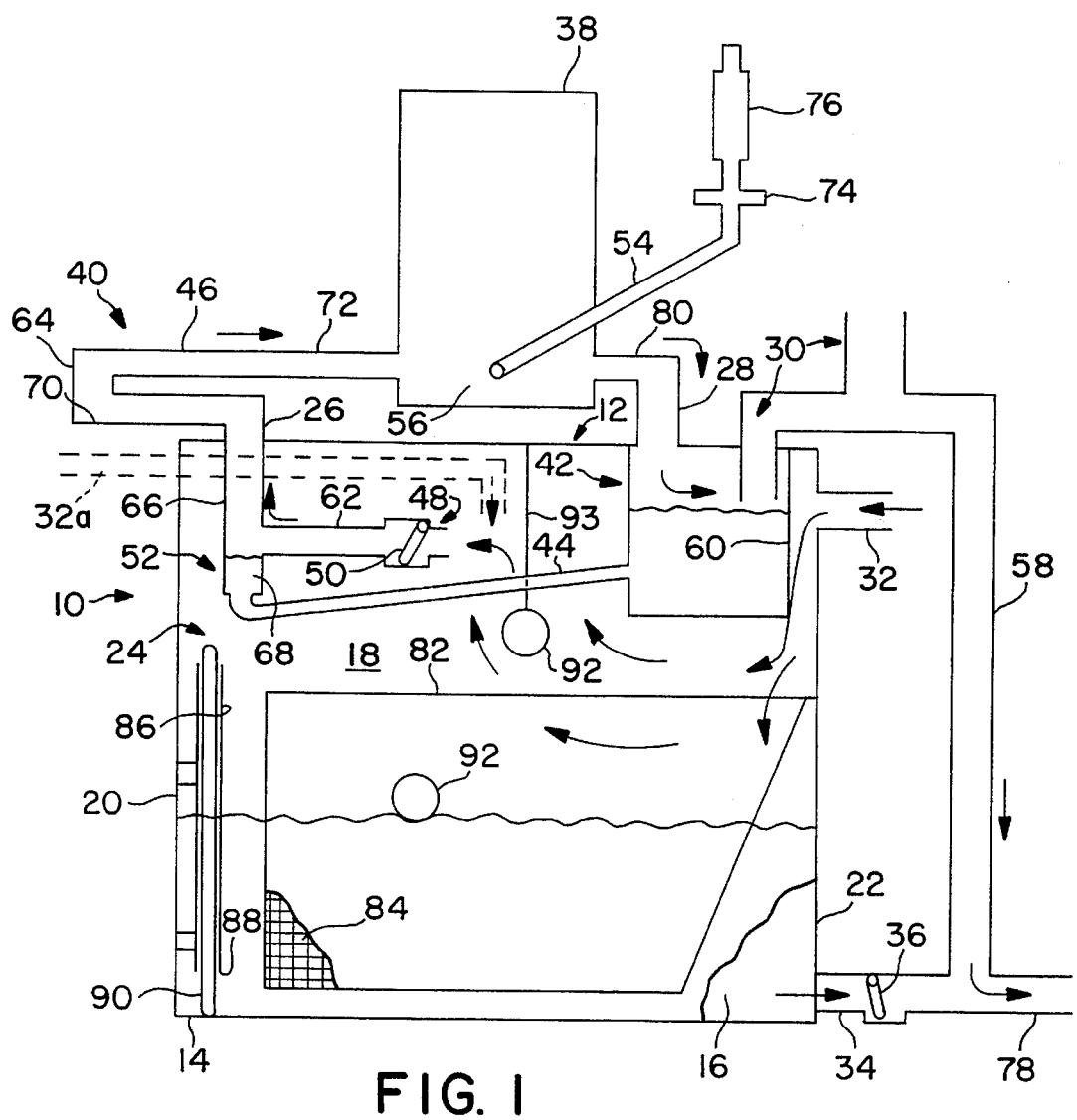
FIG. 1 is a schematic view of a water recycling and waste disposal system for dental operatories according to the invention.

Referring now to FIG. 1, the present invention comprises a collection tank 10 of robust construction with a top cover 12, bottom 14, front 16, rear 18, and left 20 and right 22 side walls defining a collection chamber 24. The tank may also be cylindrical. The tank is constructed to function under interior partial vacuum operating conditions of up to a maximum of 24" Hg and with a normal operating vacuum of 11" to 15" Hg. A non-corrosive material such as fiberglass, plastic (polyvinylchloride, for example) or stainless steel is preferred. The tank is impervious except for five connections: inlet 26 and outlet 28 connections for a seal water recirculating system, a gas vent 30, an inlet 32 for operatory effluent, and an effluent drain 34. The drain is fitted with a one-way check valve 36 which is drawn closed when the tank is evacuated by the vacuum pump, and which is free to open when the vacuum pump is secured after a day's operations.

The system includes a water seal vacuum pump 38 with a closed seal water recirculating circuit 40, a gas—water separator 42 of sufficient capacity to serve as a reservoir, a return line 44, and an inlet line 46 for directing seal water to the pump. As illustrated in FIG. 1, the outlet exhaust line 28 and the gas vent line 30 pass through the top wall 12 of the tank thereby locating the separator 42 and the return line 44 inside the collection chamber 24. The water seal circuit is provided with an air inlet 48 through a check valve 50 at the junction 52 of the return 44 and inlet lines 48. A fresh water make-up feed line 54 supplies replenishment water directly to the pump water seals 56. The reservoir/gas—water separator is provided with gas vent 30 for exhausting air to ambience through a drain line 58. Any excess seal water from the closed circuit will pass through the drain line.

The operatory effluent inlet 32 is located adjacent the separator 42 near the top of the collection tank so that the separator wall 60 acts as a baffle diverting effluent flow downwardly into the tank and also inhibiting flow of liquid and solid components of the effluent into the air inlet 48. An alternate effluent inlet configuration 32a is also shown in the drawing.

The air inlet 48 itself is positioned in the tank to accommodate the one-way check valve 50 and providing a horizontal length of tubing 62 for entrance of evacuated air into the seal water recirculating line 64. At the end of a day's operation when the vacuum pump is shut down, the residual vacuum within the collection tank exerts a pull on the recirculating water in the closed circuit. The one-way check valve closes under the pull of the residual vacuum and prevents suction and loss of the recirculating water into the collection tank. Under this transient partial vacuum condition, the collection tank will continue to pull vacuum from the operatory hoses through inlet 32 until atmospheric pressure is established in the collection chamber.

The air inlet tube 62 joins a vertical section 66 of the recirculation circuit above a well 68 supplied with recirculating water from the reservoir by the return line 44. The vertical section extends through the tank top 12 and joins a first horizontal section 70 of the recirculating inlet followed by a second or entry horizontal section 72 into the vacuum pump 38. The vertical rise is an important aspect of the invention in that evacuated cooling air entering the inlet pipe induces an upward flow of water particles from the well through the vertical section with prolonged intimate contact of water and air for efficient heat transfer from water to air through the vertical rise and the first and second horizontal sections. The inlet comprising vertical and horizontal sections constitutes a heat exchanger in which the operating temperature and vapor pressure of recirculating water is reduced before entering the pump thereby providing for optimum operating efficiency of the vacuum pump. For example, the water collecting at the reservoir at pump outlet is very warm, say approximately 140 F. After transiting the heat exchanger, the water is cooled substantially to slightly above room temperature for providing a recirculated water seal. The heat exchanger is illustrative of one suitable for accomplishing the objects of the invention it being understood that other heat exchanger configurations for transfer of evacuated air to recirculating water will occur to those skilled in the art and may be used with the invention.

A make-up feed line 54 connects directly to the vacuum pump and is fitted with a flow regulator 74 and an optional pressure regulator 76 which together determine the amount of make-up water allowed into the system. When used with the invention, the orifice plate flow restrictor and pressure regulator are selected and set to provide a preferred flow rate of between 1 and 1.5 gallons per hour or 3 gallons per hour when the flow restrictor is used alone.

The gas—water separator 42 shown in FIG. 1 receives the water and air outlet flow from the vacuum pump for collecting the water and venting the air to ambience via vent 30 and water via line 58 to a plumbing drain 78. The reservoir is of sufficient capacity to handle the water flow of approximately 30 gallons per hour consisting approximately of 1–3 gallons per hour of fresh make-up water and 27–29 gallons per hour of recirculating water. This reservoir capacity is suitable for a conventional 1 hp vacuum pump having an air flow of 17 cfm at 11" Hg., as well as twin 1 hp and twin 2 hp vacuum pump systems. The interior configuration of the reservoir provides for separating the inflow line 28 from the vent line 30 and for positioning the outflow line just above the normal reservoir water level. The lower level in the separator for the opening of the vent-drain line 30 is useful in case of malfunction to direct excess water to drain via line 58.

In addition, the diameter of the discharge line 80 immediately out of the pump is considerably smaller in diameter (1½", e.g.) than the diameter (6") of the reservoir. This change in flow line diameter allows the air exiting the vacuum pump to reduce its velocity. The result is a smooth relatively quiescent air flow along the water surface through the reservoir to the vent line thereby minimizing blow-by or carry-over of recirculating water from the reservoir to the drain.

The gas/water separator by controlling the flow of air to the vent line, limits blow-by (i. e., carriage of water drops by the air into the vent and drain line) and ensures an adequate amount of recirculation water is available at all times.

In operation, the vacuum pump draws a vacuum in the collection tank through the air inlet check valve. The tank is connected to dental office operatories through the effluent inlet so that evacuating tubes (not shown) placed in patients' mouths draw the effluent into the tank. Air drawn through the evacuating tubes into the tank enters the inlet at room temperature for cooling the recirculating seal water as it flows up and along the inlet line. The air evacuated is ported to atmosphere after passing through the pump while the recirculating water is returned to the pump via reservoir, return line, well and inlet heat exchanger. The cooled recirculation water is augmented by fresh water through the make-up line.

In order to recover portions of effluent, a porous member or sieve 82 is placed within the collection tank beneath the inlet pipe 32. The porous member includes a screen of mesh 84 selected to pass liquid and fines such as the fine grit or pumice used for polishing teeth. Coarser material such as heavy metal and amalgam is retained by the mesh screen for periodic removal and recovery of material of value or to avoid environmentally improper disposal of harmful materials. To accomplish this, the tank may be formed in upper and lower sections for disassembly and removal of the screen.

In another aspect of the invention, a vertical tube 86 is secured inside the tank and provided with an open end 88 at the bottom of the tank serving as a dispenser. A rod or a stack of tablets 90 made of suitable disinfectant may be supported in the tank by the tube in exposure to effluent for gradual dissolution and release of disinfectant in amounts to disinfect each batch of effluent received in the tank. Chlorine tablets such as are used for disinfecting and winterizing swimming pools may be acceptable for this purpose in the collection tank.

A floating light weight rigid ball 92 is deployed within the collection tank to guard against entry of effluent into the air inlet 48 and into the heat exchanger. The ball may be deployed by flotation on the surface of effluent or may be suspended by a tether 93 from the top cover 12 of the tank. The ball will rise with an increasing effluent level and be drawn into contact with the inlet preventing entry of effluent into the heat exchanger and mixing with recirculation water.

Figure 2:
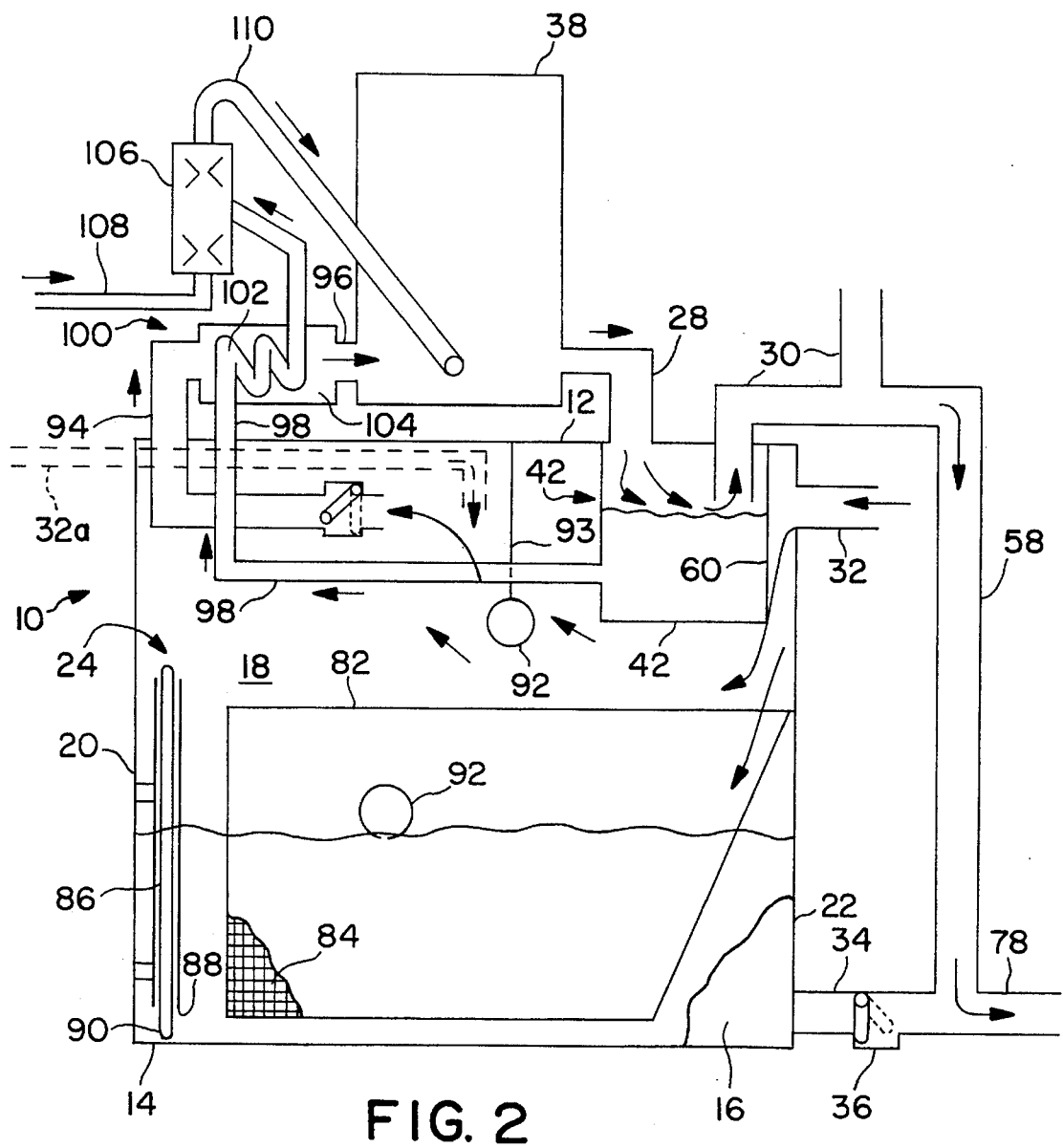
FIG. 2 is a schematic view of a modified water recycling and waste disposal system for dental operatories according to the invention.

A modified form of the invention is illustrated in FIG. 2, and utilizes the same reference numerals as FIG. 1 for the same components. In this arrangement, a collection tank 10 of construction similar to the tank of FIG. 1 is fitted with an inlet pipe 32 for receiving effluent from operatories. A drain line 78 with check valve 36 as in the embodiment of FIG. 1 is also provided. A third tank fitting comprises an air inlet tube 94 connected to the suction side 96 of the vacuum pump.

The water seal arrangement for the vacuum pump includes an air-water separator 42 for seal water connected to the outlet 28 of the vacuum pump and located within the collection chamber 24 as in FIG. 1. The separator 42 vents entrained air and gas to atmosphere through gas vent 30 and drain line 58. The recirculating seal water flows through a return line 98 to an air/water heat exchanger 100 where air at room temperature is drawn by the vacuum pump from the operatories via the collection tank and passes over a cooling coil 102 in the return line 98 and forming part of a heat exchanger 104 for returning the recirculating water back to desired limits of temperature and vapor pressure. The warmed cooling air enters the vacuum pump and is thereafter ported to ambience through line 28, the separator 42, vent 30, and the drain line 58. The recirculated seal water flows to an eductor 106 under the influence of pressurized fresh make-up water arriving at the eductor by fresh water line 108. The result is a commingled flow of cooled recirculating seal water and tap water to provide a water seal for the vacuum pump through seal water supply line 110. With this arrangement the need to use make-up feed water for cooling the recirculating water is minimized through use of cooling air from the collection tank. A flow restrictor such as an orifice plate together with a pressure regulator may be included in the fresh water line 108 to control water consumption at a rate required for eductor operation and maintaining seal water volume in the recirculating system.

As in the case of FIG. 1, the modified embodiments of FIGS. 2–8 may also be furnished with a reclamation or salvage screen 82 for retrieving components of the operatory effluent. The modified embodiments may also be provided with suitable disinfecting means 86 suspended within the collection tank.

For ease and clarity of description, the modified embodiments of FIGS. 3–8 are described collectively to the extent they incorporate the same or similar components with corresponding reference numerals as the embodiment of FIG. 1, and are described individually where distinct components are shown.

In the embodiments of FIGS. 3–6, each collection tank 10 is of robust construction with a top cover 12, bottom 14, front 16, rear 18, and left 20 and right 22 side walls defining a collection chamber 24 to function under interior partial vacuum operating conditions of up to a maximum of 24" Hg and with a preferable operating vacuum range of 11"to 15" Hg, with 12" Hg as the normally desired setting. Each tank 10 is impervious except for the following connections: inlet 26 and outlet 28 connections for a seal water recirculating system, a gas vent 30 (FIGS. 5, 6, and 7), an inlet 32 for operatory effluent, and an effluent drain 34. The drain is fitted with a one-way check valve 36 which is drawn closed when the tank is evacuated by the vacuum pump, and which is free to open when the vacuum pump is secured after a day's operations.

The system in each of FIGS. 3–6 includes a water seal vacuum pump 38 with a closed seal water recirculating circuit 40, a gas-water separator 42, a reservoir 43 of sufficient capacity to serve as a well for recirculating seal water, a return line 44, and an inlet line 46 for directing seal water to the pump. The water seal circuit is provided with an air inlet 48 through a check valve 50 at the junction 52 of the return 44 and inlet lines 48. A fresh water make-up feed line 54 supplies replenishment water directly to the pump water seals 56. The gas-water separator 42 is provided with gas vent 30 for exhausting evacuated air and entrained gas such as nitrous oxide to ambience. Any excess seal water from the closed seal water recirculating circuit will pass through the drain line 58 through a float valve 59 located in the gas-water separator. The float valve comprises a high density floatable rubber ball for maintaining a water level above the drain inlet 58a so as to preclude the flow of evacuated air and entrained gas through the drain line. The ball float valve provides very positive and complete separation of gas and water components included in the outflow from the vacuum pump. The ball float valve allows excess seal water only to enter the plumbing drain in that the ball 59a closes the valve when there is low water in the valve housing 59b so that none of the evacuated air with entrained nitrous oxide enters the drain line 58. With a low water condition in the valve housing, the valve is closed by ball engaging the valve seat 59c so that the air/gas component of vacuum pump outflow can only rise through the vent to ambience. As excess seal water fills the valve housing, the ball floats off the valve seat opening the valve for draining the excess seal water. Excess seal water filling the valve housing while the valve is open, acts as an effective barrier to air/gas flow through the valve to drain. In this way, the ball float valve provides positive and complete separation of gas and water regardless of variations in the respective volumes of the gas and water constituents in the vacuum pump outflow.

The operatory effluent inlet 32 is located near the top of the collection tank preferably diverting effluent flow downwardly into the tank and also inhibiting flow of liquid and solid components of the effluent into the air inlet 48.

The air inlet 48 itself is positioned in the tank to accommodate the one-way check valve 50 and provides a horizontal length of tubing 62 for entrance of evacuated air into the seal water recirculating line 46. The one-way check valve closes under the pull of the residual vacuum and prevents suction and loss of the recirculating water into the collection tank under transient partial vacuum conditions described above in connection with FIG. 1.

The air inlet tube 48 joins a vertical section 66 of the recirculation circuit above a well 68 supplied with recirculating water from the reservoir by the return line 44. The vertical section 66 extends through additional piping 67 into the vacuum pump 38. As pointed out in connection with the embodiment of FIG. 1, the vertical rise is an important aspect of the invention and is included in the embodiments of FIGS. 3–8 so that evacuated cooling air entering the inlet pipe induces an upward flow of water particles from the well through the vertical section with prolonged intimate contact of water and air for efficient heat transfer from water-to-air through the vertical rise and horizontal section. The inlet comprising vertical and horizontal sections constitutes a heat exchanger in which the operating temperature and vapor pressure of recirculating water is reduced before entering the pump thereby providing for optimum operating efficiency of the vacuum pump. The heat exchanger is illustrative of one suitable for accomplishing the objects of the invention it being understood that other heat exchanger configurations for transfer of evacuated air to recirculating water will occur to those skilled in the art and may be used with the invention.

Figure 3:
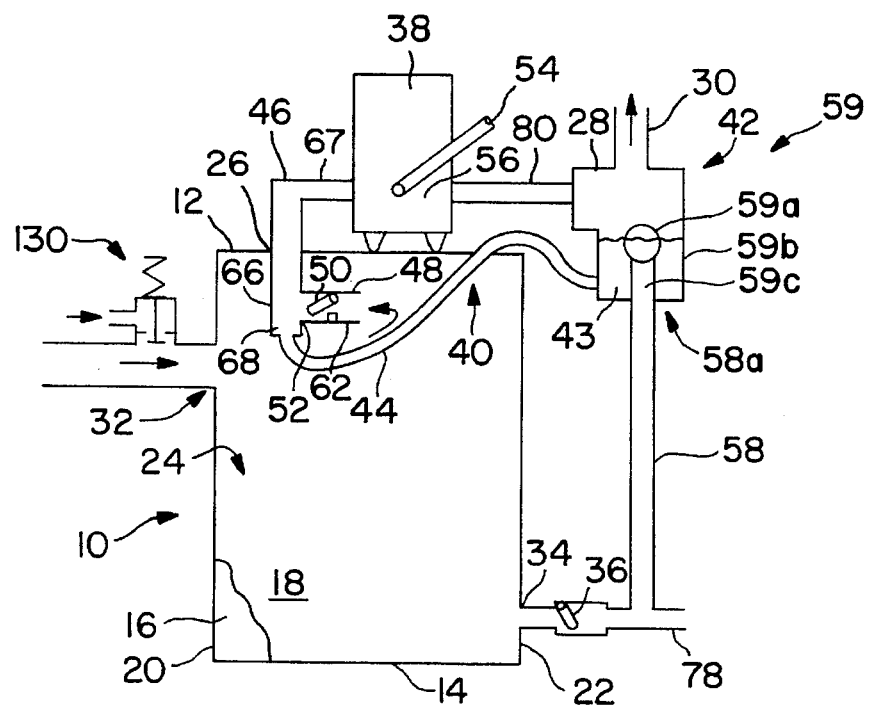
FIG. 3 is a schematic view of a modified water recycling and waste disposal system for dental operatories according to the invention which includes vacuum relief for the collection tank and its inlet vacuum line, and a gas-water separator with float valve structurally apart from the collection tank.
Figure 4:
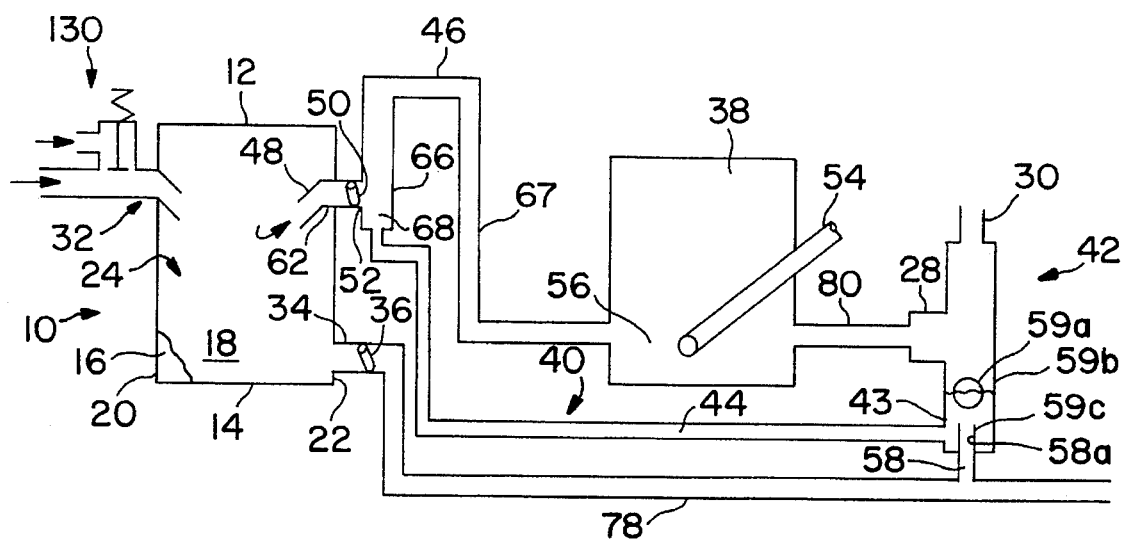
FIG. 4 is a schematic view of a modified water recycling and waste disposal system for dental operatories according to the invention which includes vacuum relief and cyclonic flow for the collection tank, a remote collection tank and an independent gas-water separator with float valve.

The gas—water separator 42 shown in FIGS. 3 and 4 receives the water and air outlet flow from the vacuum pump for collecting the water and venting the air to ambience via vent 30. Water collects in the reservoir 43 with excess recirculating water flowing via a float valve 59 and line 58 to a plumbing drain 78. The reservoir is of sufficient capacity to handle the water flow of approximately 30 gallons per hour consisting approximately of 1–3 gallons per hour of fresh make-up water and 27–29 gallons per hour of recirculating water. This reservoir capacity is suitable for a conventional 1 hp vacuum pump having an air flow of 17 cfm at 11" Hg., as well as twin 1 hp and twin 2 hp vacuum pump systems. The interior configuration of the separator 42 provides for separating the inflow line 28 from the vent line 30 and for positioning the outflow line 58a just below the normal water level in reservoir 43.

In addition, the diameter of the discharge line 80 immediately out of the pump is considerably smaller in diameter than the diameter of the separator inlet 28. This change in flow line diameter allows the air exiting the vacuum pump to reduce its velocity. The result is a smooth relatively quiescent air flow through the separator to the vent line thereby minimizing blow-by or carry-over of recirculating water. The air-water separator by controlling the flow of air to the vent line, limits blow-by (i. e., carriage of water drops by the air into the vent and drain line) and ensures an adequate amount of recirculation water is available at all times.

Figure 5:
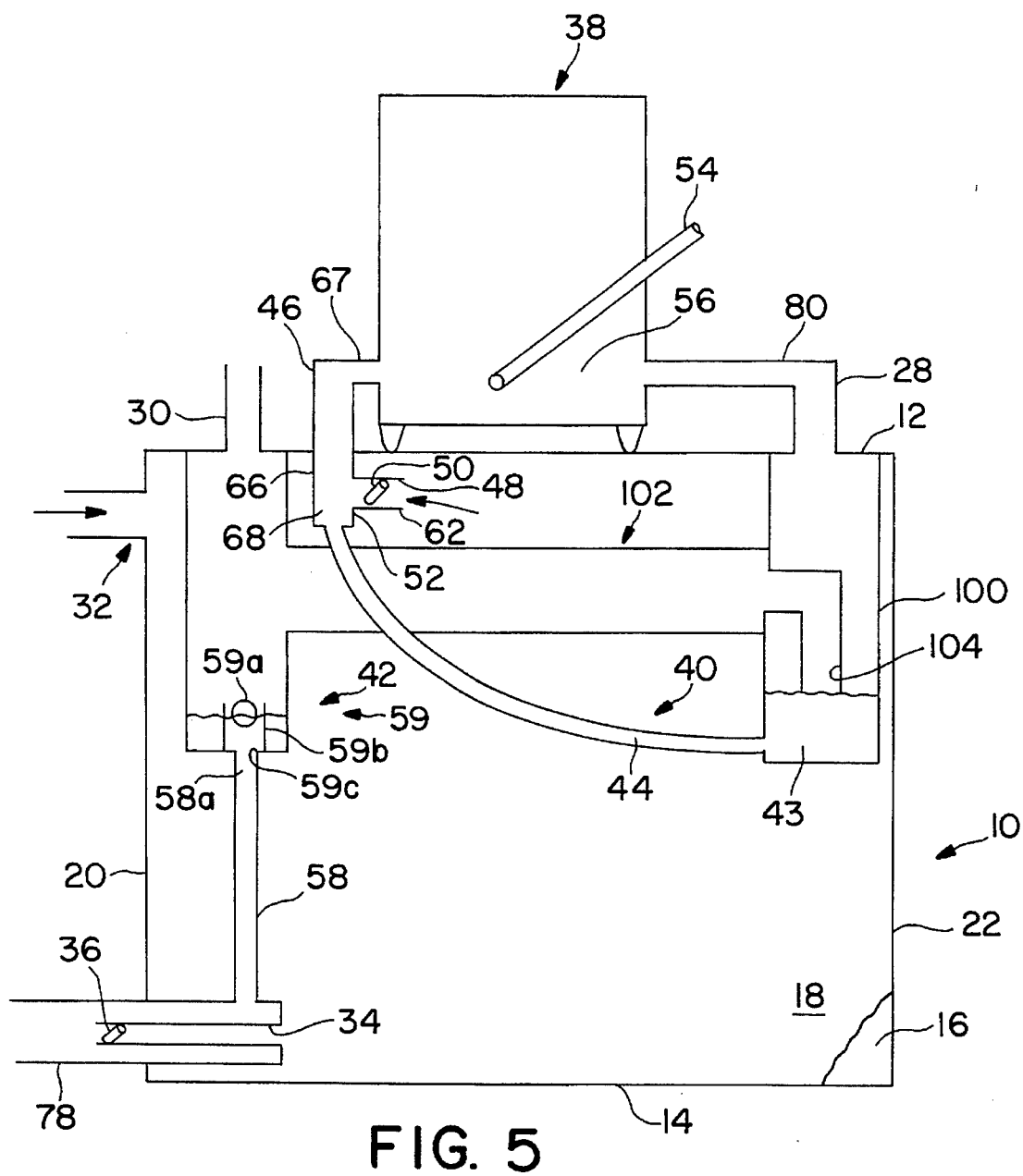
FIG. 5 is a schematic view of a modified water recycling and waste disposal system for dental operatories according to the invention which includes an articulated reservoir and gas-water separator with float valve located within the collection tank.

The gas-water separator 42 shown in FIG. 5 receives the water and air outlet flow from the vacuum pump through lines 80 and 28, receiving chamber 100 and enclosed air-water channel 102. The receiving chamber serves as a reservoir which collects recirculating water in well 43. The air-water channel has an entry opening 104 located at a predetermined level within the receiving chamber for directing the outflow of evacuated air and removing seal water in excess of the desired volume in the well 43. The separator vents evacuated air to ambience via vent 30 and excess recirculating water via float valve 59 and line 58 to a plumbing drain 78. The reservoir is of sufficient capacity to handle the water flow of approximately 30 gallons per hour as above. The recirculating line 44 extends directly from the reservoir well 43 to the heat exchanger well 68.

As above, the diameter of the discharge line 80 immediately out of the pump is considerably smaller in diameter than the diameter of inlet line 28 to the receiving chamber 100.

Figure 6:
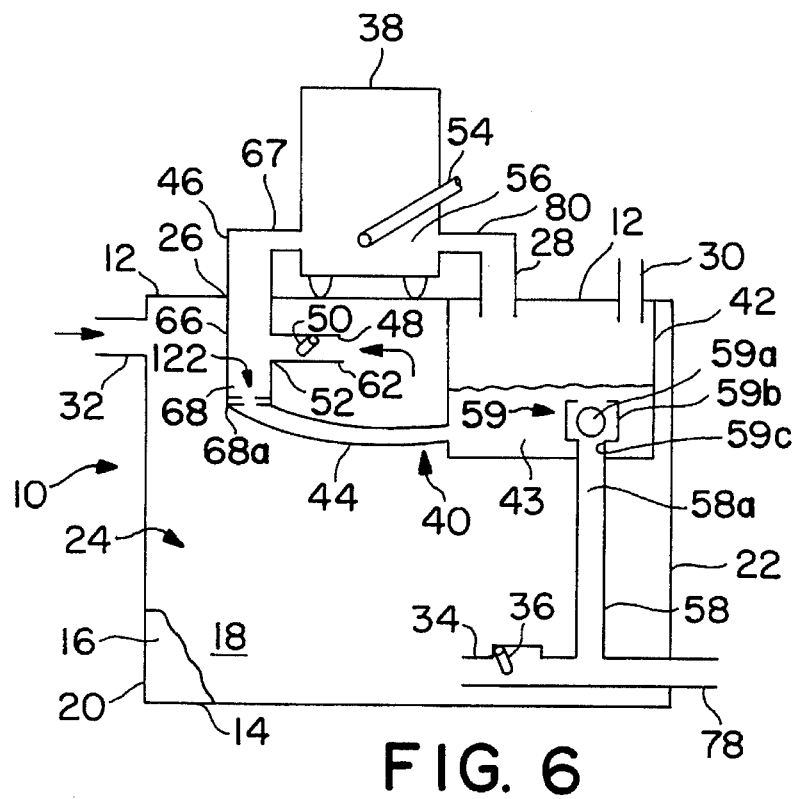
FIG. 6 is a schematic view of a modified water recycling and waste disposal system for dental operatories according to the invention which includes a metering valve for recirculating seal water at the inlet of the air-water heat exchanger, and float valve control for discarding excess seal water.

The gas—water separator 42 shown in FIG. 6 receives the seal water water and evacuated air outlet flow from the vacuum pump via lines 80, 28 for collecting the water and venting the air to ambience via vent 30. The separator includes a seal water well 43 for maintaining a desired water level determined by location of float valve 59. Excess seal water flows via float valve and line 58 to a plumbing drain 78. The reservoir is of sufficient capacity to handle the water flow of approximately 30 gallons per hour as above. The interior configuration of the reservoir provides for separating the inflow line 28 from the vent line 30 and for positioning the outflow line 58a just above the normal reservoir water level. A return line 44 leads from separator well 43 directly to the well 68 of the heat exchanger. As illustrated in FIG. 6, the outlet exhaust line 28 and the gas vent line 30 pass through the top wall 12 of the tank thereby locating the separator 42 and the return line 44 inside the collection chamber 24, as in the case of FIG. 1.

In addition, the diameter of the discharge line 80 immediately out of the pump is considerably smaller in diameter than line 28 entering the separator as above in the case of FIG. 1, for example.

The gas-water separator by controlling the flow of air to the vent line, limits blow-by and ensures an adequate amount of recirculation water is available at all times in well 43.

Figure 7:
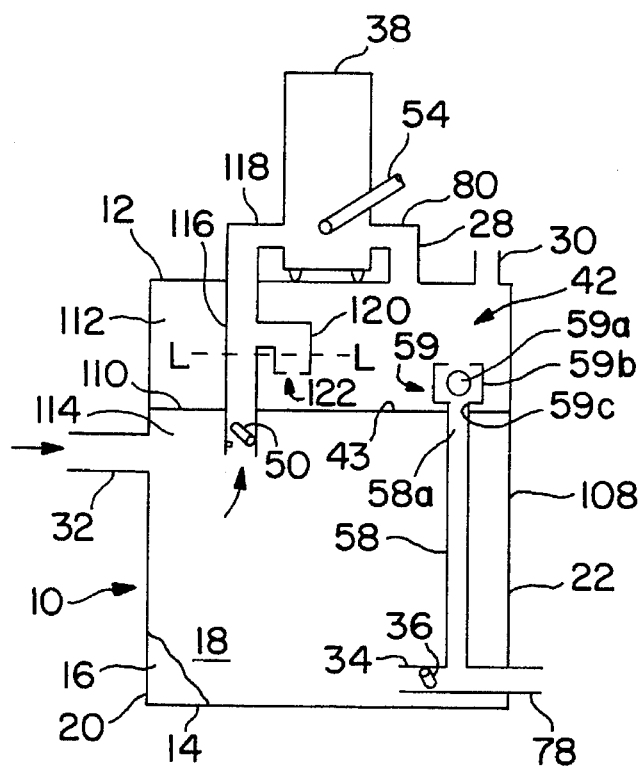
FIG. 7 is a schematic view of a modified water recycling and waste disposal system for dental operatories according to the invention which includes a collection tank divided into upper and lower chambers with the upper chamber serving as a reservoir, the lower chamber a collection tank, and with a metering valve for recirculating seal water at the inlet of the air-water heat exchanger, and float valve control for discarding excess seal water.
Figure 8:
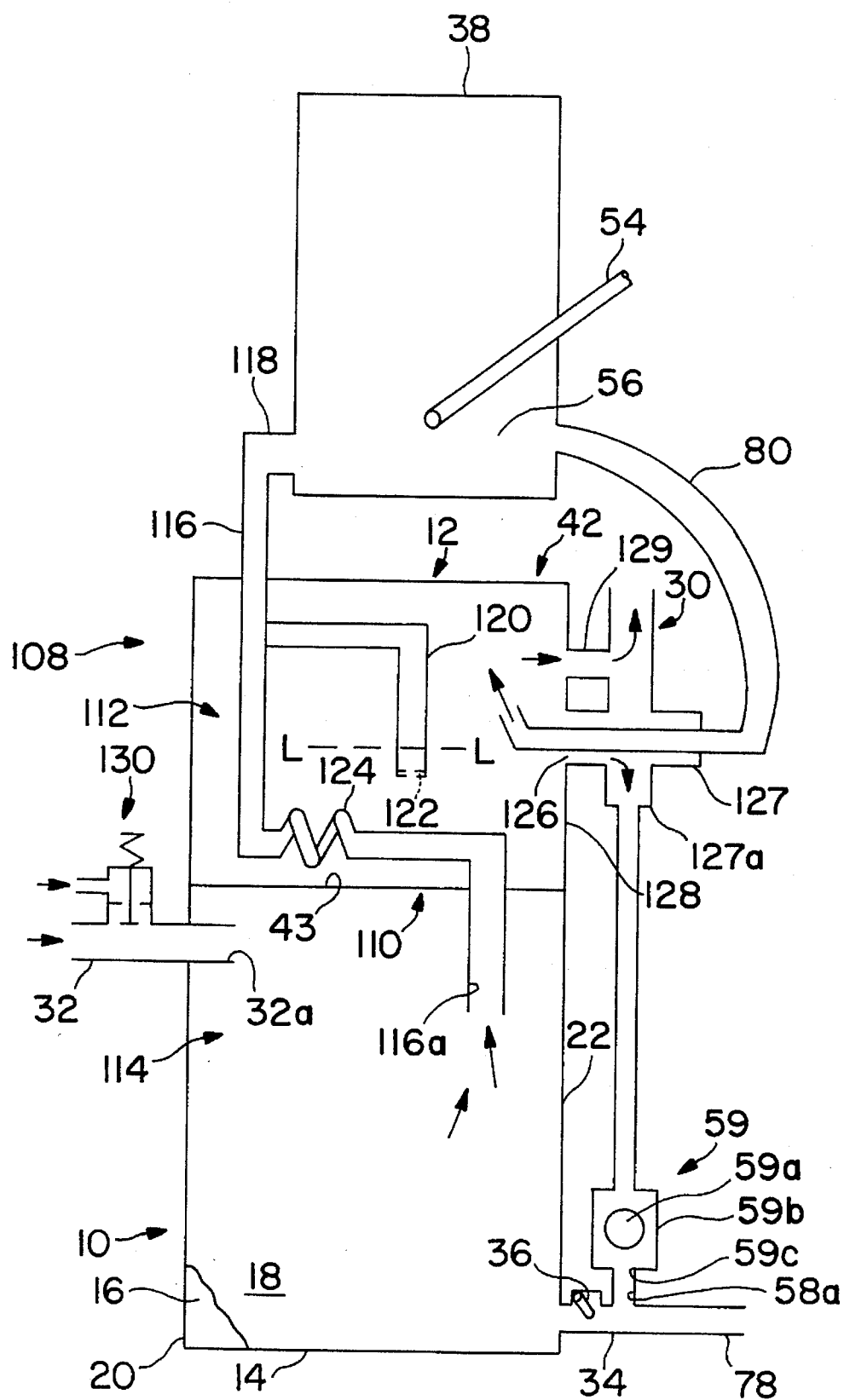
FIG. 8 is a schematic view of a modified water recycling and waste disposal system for dental operatories according to the invention which includes a collection tank divided into upper and lower chambers with the upper chamber serving as a reservoir, the lower chamber a collection tank, with a metering valve for recirculating seal water at the inlet of the air-water heat exchanger, a cooling coil in the reservoir for cooling recirculating seal water utilizing evacuated air, and air-water separator for controlling the reservoir seal water level, and float valve control for discarding excess seal water to a plumbing drain.

In the embodiments of FIGS. 7 and 8, a single tank 108 (of construction similar the that of FIG. 1 as indicated by common reference numerals) is divided by partition 110 into upper 112 and lower 114 chambers with the upper chamber serving as a combination seal water reservoir 43 and air-water separator 42 and the lower chamber serving as a evacuated collection tank.

The vacuum pump 38 is mounted atop the tank and draws air from the lower tank and from operatories through evacuation line 32 and the vertically oriented combined air inlet/air-water heat exchanger 116 and connecting pipe 118. One-way check valve 50 (omitted in FIG. 8) may be positioned at entry to the air inlet to prevent loss of seal water during transient vacuum pull by the collection tank during shutdown of the vacuum pump as noted above. The seal water inlet 120 to the air-water heat exchanger is located within the reservoir chamber below the normal water level L—L and is fitted with a metering valve 122.

In the case of FIG. 8, the one-way check valve is omitted from the air inlet because the transient vacuum pull during shutdown is very brief (e.g., 1 second or so) by reason of the small volume (e.g., 1 gallon or so) of the collection tank. There will be a some seal water drawn through the metering valve during vacuum pump shut down, however, the amount drawn is very small in respect of the volume of seal water in reservoir 43.

The vacuum pump system of FIG. 8 can be designed as two systems operating in parallel and drawing effluent from several operatories in the dental office. With this kind of installation one-way check valves must be included as a precaution in the event one of the parallel vacuum pumps is not operating.

A float valve 59 shown in FIG. 7 within the reservoir maintains the recirculating seal water within prescribed limits (i.e., above seal water inlet 120) and discards excess seal water to a plumbing drain 34. An air vent 30 opens the upper chamber to ambience to vent air evacuated by the vacuum pump. As above, the diameter of the discharge line 80 immediately out of the pump is considerably smaller in diameter than the diameter of the reservoir.

The gas-water separator by controlling the flow of air to the vent line, limits blow-by and ensures an adequate amount of recirculation water is available at all times.

In the embodiment of FIG. 8, the air line 116 to vacuum pump for evacuating the lower tank and operatories through line 32 passes through the upper chamber 112 in the form of a heat exchanger coil 124 preferably fabricated of copper for cooling recirculating seal water in the reservoir 43. Heat transfer occurs between the evacuated air at room temperature in coil 124 and recirculating seal water in the reservoir which is at approximately 140 deg. F. as noted above. Preferably inlet opening 116a of air line 116 is positioned below the entry level 32a of evacuation line 32 to minimize carry over of effluent particularly pumice into the air inlet.

The reservoir recirculating water level in the upper chamber is maintained by an air-water separator opening 126 in the upper chamber wall 128. Outflow line 80 from the vacuum pump carries evacuated air and entrained gas together with seal water through opening 126 and "T" connection 127 into the upper chamber. Excess recirculating seal water backflows through the opening 126 through a lower "T" connection 127a into float valve 59 and drain 34. An upper "T" connection 129 is also provided as the primary flow path for passing evacuated air and gas to ambience through vent 30. Some air and gas may pass to ambience through "T" connection 127, however, primary flow is through the upper "T" to minimize air blowback through opening 126 and connection 127.

Additionally, float valve 59 maintains a positive quantity of seal water over the outlet 58a to a plumbing drain to avoid air and gas venting through the plumbing drain 34.

The gas/water separator by controlling the flow of air to the vent line, limits blow-by and ensures an adequate amount of recirculating seal water is available at all times.

In each of the embodiments of FIGS. 6, 7 and 8, the metering valve 122 is in the form of an orifice plate. The metering valve is located in FIG. 6 at the entry 68a to the seal water well leading to the air-water heat exchanger 66, and in FIGS. 7 and 8 at seal water inlet 120.

The embodiments of FIGS. 3, 4 and 8 are provided with vacuum relief valves 130 at the evacuating line between the operatories and the collection tank. The relief valve is preferably spring loaded to maintain on operating vacuum range of from 11" Hg to 15" Hg, and normally at 12" Hg. The relief valve will open at 15" Hg and close at 11" Hg. The vacuum pump is capable of drawing 24" Hg, which provides a vacuum draw much too strong for oral comfort, especially if just one dental operatory is in use at a given time. The vacuum relief valve limits high vacuum to a tolerable 15" Hg level. As a practical matter under normal dental office operating circumstances, the relief valve will be open most of the time as it maintains the desired vacuum range.

In the embodiment of FIG. 8, the collection tank is small and the float valve 92 of FIGS. 1 and 2 is omitted. As a result, there may be some carryover of grey water into the air inlet 116a and up into the pump seals. The grey water entering the air inlet is purged of effluent solids including pumice because of the effluent flow pattern within the tank before grey water carryover enters the air inlet.

It is to be appreciated that the present invention provides a simplified arrangement for providing seal water recirculation and cooling in a manner as to entirely avoid the employment of gray water separated from the operatory effluent. In addition the invention provides a significant reduction in consumption of make-up feed water in comparison to gray water systems. By organizing the system around an evacuated collection tank the invention utilizes a cooling medium (air) of substantially constant, i.e. room, temperature, simplifies disposal of effluent by providing reliable automatic, gravity disposal at the end of an operating day when the vacuum pump is secured and effluent flows to drain through a check valve. The tank is of sufficient capacity to handle daily effluent from several operatories with end-of-day disposal. In addition a recovery screen may remain for longer periods measured in months according to the volume of material accumulated before cleaning becomes necessary.

An important benefit of the invention is the use of seal water without adding gray water which carries entrained abrasives not removed by screens and filters employed in conventional gray water systems. The entrained abrasives are detrimental to seal integrity and cause wear of the seals and gradual loss of vacuum capacity of the pump.

It will be apparent to those skilled in the art that there are other configurations of water-to-air heat exchangers for achieving the same results as those shown and described herein, as for example a radiator used for automotive applications.

I claim:

1. A water seal recirculating system used for evacuating oral cavity effluent from dental operatories comprising a collection tank, a vacuum pump having a seal water inlet and a seal water outlet, at least one tube extending from the tank to an operatory for conveying effluent to the tank, the vacuum pump having means communicating with the tank for drawing air from the tank thereby creating a partial vacuum in the tank and establishing a vacuum pull for effluent from the operatory through the at least one conveying tube, a recirculating line which receives seal water from the seal water outlet of the vacuum pump and returning the seal water to the seal water inlet to the vacuum pump, means for directing the air drawn by the vacuum pump from the tank in heat transfer relationship with seal water in the inlet to the vacuum pump, means for augmenting the volume of recirculating seal water with tap water, and means for periodically emptying effluent collected in the tank.

2. A water seal recirculating system as defined in claim 1 in which cooling air is ported to atmosphere after passing through the vacuum pump, and gas entrained in the seal water is vented to atmosphere after exiting the pump seals.

3. A water seal recirculating system as defined in claim 1 in which air drawn by the vacuum pump maintains the temperature and vapor pressure of the recirculating seal water within prescribed limits for optimum vacuum pump performance.

4. A water seal recirculating system as defined in claim 1 in which the means for emptying the tank comprises a one-way check valve which is drawn closed by evacuating air from the collection tank and which opens to drain effluent when the tank is at atmospheric pressure.

5. A water seal recirculating system as defined in claim 1 in which a removable sieve is located in the tank for collecting solids from operatory effluent.

6. A water seal recirculating system as defined in claim 1 in which the means communicating the tank to the vacuum pump includes a check valve.

7. A water seal recirculating system as defined in claim 1 in which a disinfectant is added to the collection tank.

8. A water seal recirculating system used for evacuating oral cavity effluent from dental operatories comprising a collection tank having top and bottom walls and a side wall structure defining a collection chamber, a vacuum pump having a seal water inlet and a seal water outlet, at least one tube extending from the tank to an operatory for conveying effluent to the tank, the vacuum pump having an air inlet line communicating with the tank for drawing air from the tank thereby creating a partial vacuum in the tank and establishing a vacuum pull for effluent from the operatory through the conveying tube, a seal water recirculating system for the vacuum pump including a recirculating line for receiving seal water from the seal water outlet of the vacuum pump and returning the seal water to the seal water inlet of the vacuum pump, a gas/water separator forming part of the recirculating system and having an inlet opening for receiving the outflow of air and seal water from the vacuum pump outlet and for directing the air to ambience and the seal water to the inlet of the vacuum pump, the recirculating line forming part of the recirculating system for receiving return seal water from the separator, for receiving an inflow of air from the tank and for directing the air and water flows in heat transfer relationship so that the air cools the recirculating water moving to the vacuum pump inlet, means for augmenting the volume of recirculating seal water with fresh water, and means for periodically emptying effluent collected in the tank.

9. A water seal recirculating system as defined in claim 8 in which the recirculating line includes a vertical section located within the tank and having a well at its lower end for receiving return seal water from the separator, the vertical section further having an opening above the well for receiving an inflow of air from the tank and for directing a commingled flow of return water and tank air vertically upward in intimate prolonged contact so that the air cools the return water as they flow to the pump inlet through the recirculating line.

10. A water seal recirculating system as defined in claim 9 in which an air inlet line is located within the tank and fitted with a check valve for directing tank air to the vertical section opening.

11. A water seal recirculating system as defined in claim 9 in which the recirculating line includes a length of horizontal piping for receiving the air and water flow from the vertical section and directing the flow to the inlet side of the vacuum pump.

12. A water seal recirculating system as defined in claim 11 in which the vertical section projects through the top wall of the tank where it joins the horizontal piping.

13. A water seal recirculating system as defined in claim 8 in which the gas/water separator is enclosed, is located in the collection chamber and is of sufficient capacity to function as a reservoir for return seal water received from the vacuum pump.

14. A water seal recirculating system as defined in claim 13 which includes a line from pump outlet to separator inlet opening for directing the outflow of air and seal water from the pump to the separator with line increasing in diameter as the outflow approaches the separator thereby reducing the velocity of air entering the separator reservoir, and which further includes a gas vent line for directing the air to ambience, the gas vent line having a point of entry in the separator located at a lower level than the separator inlet opening, and a drain line for outflow of any excess water in the reservoir.

15. A water seal recirculating system as defined in claim 14 in which the gas vent ports to ambience.

16. A water seal recirculating system as defined in claim 13 in which the separator is located in the collection chamber adjacent the effluent inlet for directing the effluent toward the bottom of the tank.

17. A water seal recirculating system as defined in claim 16 in which the collection tank includes a drain line with a check valve which closes when the tank is evacuated and which is opened by accumulated effluent in the tank when the tank is at atmospheric pressure.

18. A water seal recirculating system as defined in claim 8 in which the gas/water separator is enclosed, is located in the collection chamber and which further includes a line from pump outlet to separator inlet opening for directing the outflow of air and seal water from the pump to the separator with said line increasing in diameter as the outflow approaches the separator thereby reducing the velocity of air entering the separator reservoir, and which further includes a gas vent line for directing the air to ambience, the gas vent line having a point of entry in the separator located at a lower level than the separator inlet opening so that the separator acts as a muffler for vacuum pump exhaust.

19. A water seal recirculating system as defined in claim 8 in which the augmenting means includes a pressure regulator and orifice plate cooperating to determine the volume of fresh water entering the system.

20. A water seal recirculating system used for evacuating oral cavity effluent from dental operatories comprising a collection tank having top and bottom walls and a side wall structure defining a collection chamber, a vacuum pump having a seal water inlet and a seal water outlet, at least one tube extending from the tank to an operatory for conveying effluent to the tank, the vacuum pump having an air inlet line communicating with the tank for drawing air from the tank thereby creating a partial vacuum in the tank and establishing a vacuum pull for effluent from the operatory through the conveying tube, a seal water recirculating system for the vacuum pump for receiving seal water from the seal water outlet of the vacuum pump and returning the seal water to the seal water inlet to the vacuum pump, a gas/water separator forming part of the recirculating system and having an inlet opening for receiving the outflow of air and seal water from the vacuum pump and for directing the air to ambience and the water to the vacuum pump inlet, a recirculating line forming part of the recirculating system for receiving return seal water from the separator, a heat exchanger for receiving and cooling the return seal water, the air inlet line for directing air through the heat exchanger for cooling seal water as the air flows to the vacuum pump, an eductor having a supply of pressurized fresh water for drawing the return seal water from the recirculating line and establishing a flow of commingled fresh and return seal water to the vacuum pump seal, and means for periodically emptying effluent collected in the tank.

21. A water seal recirculating system used for evacuating oral cavity effluent from dental operatories comprising a collection tank, a vacuum pump having a seal water inlet and a seal water outlet, at least one tube extending from the tank to an operatory for conveying effluent to the tank, the vacuum pump having an air inlet line communicating with the tank for drawing air from the tank thereby creating a partial vacuum in the tank and establishing a vacuum pull for effluent from the operatory through the at least one conveying tube, a recirculating line which receives seal water from the seal water outlet of the vacuum pump and returns the seal water to the seal water inlet to the vacuum pump, the air inlet line for directing the air from the tank through a vertical rise in heat transfer relationship with seal water in the inlet to the vacuum pump, means for augmenting the volume of recirculating seal water with tap water, and means for periodically emptying effluent collected in the tank.

22. A water seal recirculating system used for evacuating oral cavity effluent from dental operatories comprising a collection tank, a vacuum pump having a seal water inlet and a seal water outlet, at least one tube extending from the tank to an operatory for conveying effluent to the tank, the vacuum pump having an air inlet line communicating with the tank for drawing air from the tank thereby creating a partial vacuum in the tank and establishing a vacuum pull for effluent from the operatory through the at least one conveying tube, an air-water separator for receiving evacuated air and seal water through the outlet from the vacuum pump, the separator being an enclosed chamber having a open vent for releasing evacuated air to ambience and having a well for collecting received seal water, valve means for maintaining the seal water at a predetermined level in the well and for discarding excess water to a drain, a recirculating line which receives seal water from the separator well and returns the seal water to the seal water inlet to the vacuum pump, means for directing the air drawn from the tank in heat transfer relationship with seal water in the inlet to the vacuum pump, means for augmenting the volume of recirculating seal water with tap water, and means for periodically emptying effluent collected in the tank.

23. A water seal recirculating system as defined in claim 22 in which the air-water separator is apart from the collection tank.

24. A water seal recirculating system as defined in claim 22, which further includes vacuum relief means in the at least one tube for maintaining the partial vacuum in the system within predetermined limits.

25. A water seal recirculating system as defined in claim 22 in which the vacuum relief means maintains the system partial vacuum in a range of 11" Hg to 15" hg.

26. A water seal recirculating system used for evacuating oral cavity effluent from dental operatories comprising a collection tank, a vacuum pump having a seal water inlet and a seal water outlet, at least one tube extending from the tank to an operatory for conveying effluent to the tank, the vacuum pump having an air inlet line communicating with the tank for drawing air from the tank thereby creating a partial vacuum in the tank and establishing a vacuum pull for effluent from the operatory through the at least one conveying tube, a receiving chamber located within the collection tank for receiving the out-flow of seal water and evacuated air from the vacuum pump, a well within the receiving chamber for collecting seal water for recirculation to the vacuum pump, an enclosed air water channel having an entry opening within the receiving chamber for directing the outflow of evacuated air, the entry opening being located at a predetermined level for collected seal water and for directing excess seal water along with evacuated air through the air water channel, an air-water separator for receiving evacuated air and seal water through the channel form the receiving chamber, the separator being an enclosed chamber within the collection tank having a open vent for releasing evacuated air to ambience and having a well for collecting received seal water, valve means for maintaining the seal water at a predetermined level in the well and for discarding excess water to a drain, a recirculating line which receives seal water from the seal water well of the receiving chamber and returning the seal water to the seal water inlet to the vacuum pump, means for directing the air from the tank in heat transfer relationship with seal water in the inlet to the vacuum pump, means for augmenting the volume of recirculating seal water with tap water, and means for periodically emptying effluent collected in the tank.

27. A water seal recirculating system used for evacuating oral cavity effluent from dental operatories comprising a collection tank, a vacuum pump having a seal water inlet and a seal water outlet, at least one tube extending from the tank to an operatory for conveying effluent to the tank, the vacuum pump having an air inlet line communicating with the tank for drawing air from the tank thereby creating a partial vacuum in the tank and establishing a vacuum pull for effluent from the operatory through the at least one conveying tube, an air-water separator for receiving evacuated air and seal water through an outlet line from the vacuum pump, the separator being an enclosed chamber having a open vent for releasing evacuated air to ambience and having a well for collecting received seal water, valve means for maintaining the seal water at a predetermined level in the well and for discarding excess water to a drain, a recirculating line which receives seal water from the separator well and returns the seal water to the seal water inlet to the vacuum pump, a metering valve in the recirculating line for establishing the volume of recirculating seal water entering the seal water inlet, means for directing the air drawn from the tank in heat transfer relationship with seal water in the inlet to the vacuum pump, means for augmenting the volume of recirculating seal water with tap water, and means for periodically emptying effluent collected in the tank.

28. A water seal recirculating system used for evacuating oral cavity effluent from dental operatories comprising a tank partitioned into upper and lower chambers, a vacuum pump having a seal water inlet and a seal water outlet, at least one tube extending from the tank to an operatory for conveying effluent to the lower chamber of the tank, the vacuum pump having an air inlet line communicating with the lower chamber for drawing air therefrom thereby creating a partial vacuum in the lower chamber and establishing a vacuum pull for effluent from the operatory through the at least one conveying tube, the upper chamber of the tank defining an air-water separator for receiving evacuated air and seal water through an outlet line from the vacuum pump, the separator having a open vent for releasing evacuated air to ambience and having a well for collecting received seal water, valve means for maintaining the seal water at a predetermined level in the well and for discarding excess water to a drain, a recirculating line which receives seal water from the separator well and returns the seal water to the seal water inlet to the vacuum pump, means for directing the air drawn from the tank in heat transfer relationship with seal water in the inlet to the vacuum pump, means for augmenting the volume of recirculating seal water with tap water, and means for periodically emptying effluent collected in the tank.

29. A water seal recirculating system as defined in claim 28 which further includes a metering valve in the recirculating line for establishing the volume of recirculating seal water entering the seal water inlet.

30. A water seal recirculating system used for evacuating oral cavity effluent from dental operatories comprising a vacuum pump having a seal water inlet and a seal water outlet, a tank partitioned into upper and lower chambers, the upper chamber of the tank defining an air-water separator for receiving evacuated air and seal water through an outlet line from the vacuum pump, the separator having a open vent for releasing evacuated air to ambience and having a well for collecting received seal water, means for maintaining the seal water at a predetermined level in the well and for discarding excess water to a drain line, at least one tube extending from the tank to an operatory for conveying effluent to the lower chamber, the vacuum pump having an air inlet line communicating with the lower chamber for drawing air therefrom thereby creating a partial vacuum in the lower chamber and establishing a vacuum pull for effluent from the operatory through the at least one conveying tube, the vacuum pump air inlet line passing through the upper chamber and there defining a heat exchanger for cooling the collected seal water in the well of upper chamber, a recirculating line which receives seal water from the separator well and returns the seal water to the seal water inlet to the vacuum pump, means for directing the air drawn from the lower chamber in heat transfer relationship with seal water in the inlet to the vacuum pump, means for augmenting the volume of recirculating seal water with tap water, and means for periodically emptying effluent collected in the tank.

31. A water seal recirculating system as defined in claim 30 in which the means for maintaining the seal water at a predetermined level in the well and for discarding excess water to a drain comprises an over flow line combined with the separator vent and includes a float valve to maintain a water seal in the drain line to preclude flow of evacuated air into the drain line.

32. In a seal water recirculating system for vacuum pump water seals with the vacuum pump utilized for evacuating one or more dental operatories the improvement which comprises a reservoir tank for collecting recirculated seal water, an air inlet line to the vacuum pump for drawing air and effluent from one or more operatories, the air inlet line being directed through the reservoir tank, the air line having an opening communicating with seal water in the reservoir for drawing seal water into the air line, the air inlet line having a vertical rise for accommodating drawn air and seal water in intimate heat transfer relationship for entering the vacuum pump seals, and means for discharging seal water from the vacuum pump seals to the reservoir.

33. The improvement of claim 32 which further includes means for removing solids from the effluent.

34. The improvement of claim 33 which further includes means for removing solids from the effluent.

35. In a seal water recirculating system for vacuum pump water seals with the vacuum pump utilized for evacuating one more dental operatories the improvement which comprises a reservoir tank for collecting recirculated seal water, an air inlet line to the vacuum pump for drawing air and effluent from one or more operatories, the air inlet line being directed through the reservoir tank, a heat exchanger forming part of the air inlet line for transfer of heat from seal water in the reservoir to the drawn air in the line, the air line having an opening communicating with seal water in the reservoir for drawing seal water into the air line, the air inlet line having a vertical rise for accommodating drawn air and seal water in intimate heat transfer relationship for entering the vacuum pump seals, and means for discharging seal water from the vacuum pump seals to the reservoir.

36. In a seal water recirculating system for vacuum pump water seals with the vacuum pump utilized for evacuating one or more dental operatories the improvement which comprises a reservoir tank for collecting recirculated seal water, an air inlet line to the vacuum pump for drawing air and effluent from one or more operatories, the air inlet line being directed through the reservoir tank, a heat exchanger forming part of the air inlet line for transfer of heat from seal water in the reservoir to the drawn air in the line, the air line having an opening communicating with seal water in the reservoir for drawing seal water into the air line for accommodating drawn air and seal water in intimate heat transfer relationship for entering the vacuum pump seals, means for discharging seal water from the vacuum pump seals to the reservoir, and means for removing solids from the effluent.

* * * * *